United States Patent
Naito et al.

(10) Patent No.: US 11,273,110 B2
(45) Date of Patent: Mar. 15, 2022

(54) DYE FOR HAIR COLORATION, COMPOSITION FOR HAIR COLORATION CONTAINING DYE, AND METHOD FOR PRODUCING DYE

(71) Applicant: HODOGAYA CHEMICAL CO., LTD., Tokyo (JP)

(72) Inventors: Keigo Naito, Tokyo (JP); Tetsuya Yoshida, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 17/185,192

(22) Filed: Feb. 25, 2021

(65) Prior Publication Data

US 2021/0267861 A1  Sep. 2, 2021

(30) Foreign Application Priority Data

Feb. 27, 2020  (JP) .............................. JP2020-032481

(51) Int. Cl.
*A61Q 5/10* (2006.01)
*A61K 8/41* (2006.01)
*A61K 8/49* (2006.01)

(52) U.S. Cl.
CPC ............... *A61K 8/416* (2013.01); *A61K 8/49* (2013.01); *A61Q 5/10* (2013.01); *A61K 2800/4324* (2013.01); *A61K 2800/48* (2013.01); *A61K 2800/805* (2013.01)

(58) Field of Classification Search
CPC ...... A61Q 5/065; A61K 8/4946; A61K 8/416; A61K 8/42; A61K 8/40; A61K 8/49
USPC ........................................................... 8/426
See application file for complete search history.

(56) References Cited

U.S. PATENT DOCUMENTS

| 2013/0340182 A1 | 12/2013 | Isobe et al. |
| 2015/0101132 A1* | 4/2015 | David ................ A61Q 5/065 8/426 |
| 2016/0152831 A1 | 6/2016 | Akiba et al. |

FOREIGN PATENT DOCUMENTS

| EP | 1415643 | 5/2004 |
| WO | 2014/203771 | 12/2014 |

OTHER PUBLICATIONS

STIC Search Report dated Sep. 1, 2021.*
UK search report issued with respect to UK Patent Application No. 2102793.3, dated Oct. 14, 2021.

* cited by examiner

*Primary Examiner* — Eisa B Elhilo
(74) *Attorney, Agent, or Firm* — Greenblum & Bernstein, P.L.C.

(57) ABSTRACT

A dye for hair coloration that has a long shelf life and is excellent in heat resistance, and a method for producing the dye for hair coloration, are provided. A dye for hair coloration represented by the following general formula (1), the dye for hair coloration having a proportion of a polyatomic anion (An) or impurities derived from An of 1% by mass or less:

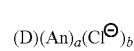

(1)

wherein in the formula (1), D represents a cationic moiety of the dye for hair coloration; An represents a polyatomic anion; and a and b each independently represent a value of 0 to 1.

20 Claims, No Drawings

DYE FOR HAIR COLORATION, COMPOSITION FOR HAIR COLORATION CONTAINING DYE, AND METHOD FOR PRODUCING DYE

TECHNICAL FIELD

The present invention relates to a dye for hair coloration, a composition for hair coloration containing the dye, and a method for producing the dye.

BACKGROUND ART

In recent years, increasing number of individuals in a wide age range are enjoying various hair colors by dyeing black hair or white hair, and many hair coloring agents, such as a hair coloring material and a hair dye, and many hair colorants, such as a hair coloring manicure and a hair coloring treatment, are being sold. In the hair coloring process, an oxidation hair coloring agent (permanent hair coloring agent), which uses an oxidation dye having high hair dyeing power and exerting good color retention, has been mainly used, but has problems of the occurrence of damage of hair and skin irritation including allergy. Under the circumstances, instead of the oxidation dye, hair colorants using a basic dye having high safety have been proposed (see, for example, PTLs 1 to 6).

An HC dye used in combination with a basic dye has been used as a semipermanent hair colorant, and for example, HC Blue 15 is being used as a blue HC dye. However, a hair colorant using HC Blue 15 has an issue in heat resistance after dyeing, and has a problem of decoloration and discoloration in the heating treatment in production and decoloration and discoloration in long-term storage and use with warm water (around 40° C.). There is a demand of dyes for hair coloration including the blue dye for hair coloration that are free of decoloration and can retain clear color.

CITATION LIST

Patent Literatures

PTL 1: JP-A-2002-37718
PTL 2: JP-A-2004-285048
PTL 3: WO 2018/180515
PTL 4: WO 2009/041514
PTL 5: WO 2013/190774
PTL 6: WO 2014/203771

SUMMARY OF INVENTION

Technical Problem

A problem to be solved by the present invention is to provide a dye for hair coloration that has a long shelf life and is excellent in heat resistance, and a method for producing the dye for hair coloration.

Solution to Problem

The present invention has been made as a result of the earnest investigations for solving the problem, and is constituted by the following contents.

1. A dye for hair coloration represented by the following general formula (1), the dye for hair coloration having a proportion of a polyatomic anion (An) or impurities derived from An of 1% by mass or less:

$$(D)(An)_a(Cl^{\ominus})_b \tag{1}$$

wherein in the formula (1), D represents a cationic moiety of the dye for hair coloration; An represents a polyatomic anion; and a and b each independently represent a value of 0 to 1.

2. The dye for hair coloration, wherein in the general formula (1), D represents a cationic moiety of a triarylmethane dye, a xanthene dye, a phenothiazine dye, a phenazine dye, a phenoxazine dye, an azo dye, an azomethine dye, or an HC dye.

3. The dye for hair coloration, wherein in the general formula (1), D is represented by the following general formula (2):

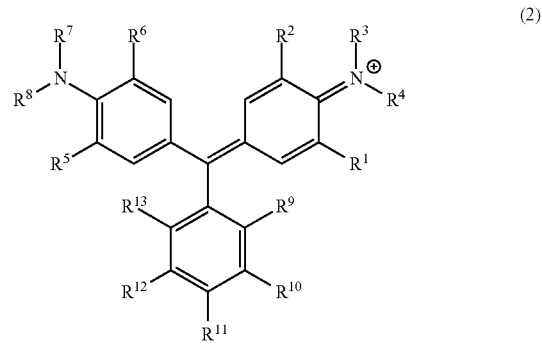

wherein in the formula (2), $R^1$ to $R^{13}$ each independently represent —H, a halogen atom, —NO$_2$, —NO, —CN, —OH, an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that adjacent groups of each combination of $R^3$ and $R^4$, $R^7$ and $R^8$, and $R^9$ to $R^{13}$ may be bonded to each other to form a ring.

4. The dye for hair coloration, wherein in the general formula (1), D is represented by the following general formula (3):

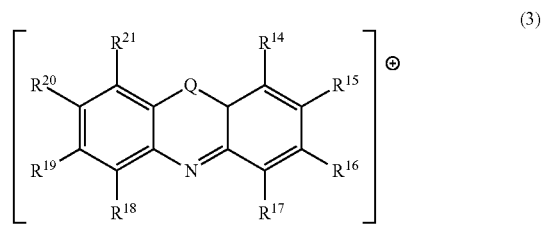

wherein in the formula (3), $R^{14}$ to $R^{21}$ each independently represent —H, a halogen atom, —NO$_2$, —NO, —CN, —OH, an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that adjacent groups of $R^{14}$ to $R^{21}$ may be bonded to each other to form a ring; and Q represents —CH=, —N=, —O—, —S—, an amino group having 0 to 30 carbon atoms, which may have a substituent, or a methylene group, which may have a substituent.

5. The dye for hair coloration, wherein in the general formula (1), D is represented by the following general formula (4):

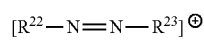 (4)

wherein in the formula (4), $R^{22}$ and $R^{23}$ each represent an amino group having 0 to 20 carbon atoms, which may have a substituent, a linear or branched alkenyl group having 2 to 20 carbon atoms, which may have a substituent, an aromatic hydrocarbon group having 6 to 30 carbon atoms, which may have a substituent, or a heterocyclic group having 2 to 30 carbon atoms, which may have a substituent.

6. The dye for hair coloration, wherein in the general formula (1), D is represented by the following general formula (5):

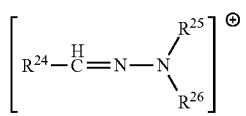 (5)

wherein in the formula (5), $R^{24}$ to $R^{26}$ each independently represent an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that $R^{25}$ and $R^{26}$ may be bonded to each other to form a ring.

7. The dye for hair coloration, wherein in the general formula (2), $R^1$, $R^2$, $R^5$, and $R^6$ each represent —H or a methyl group; $R^3$, $R^4$, $R^7$, and $R^8$ each represent —H, a methyl group, or an ethyl group; and $R^9$ to $R^{13}$ each represent —H, —Cl, an amino group having 0 to 10 carbon atoms, which may have a substituent, an alkenyl group having 2 to 10 carbon atoms, which may have a substituent, an alkyl group having 1 to 10 carbon atoms, which may have a substituent, or an acyl group having 1 to 10 carbon atoms, which may have a substituent.

8. The dye for hair coloration, wherein in the general formula (1), An represents a hydrogen-containing anion.

9. The dye for hair coloration, wherein the dye for hair coloration has a shelf life of 6 months or more at a room temperature (20 to 25° C.) or 7 days or more at 40 to 60° C.

10. A composition for hair coloration containing the dye for hair coloration, at least one kind of an auxiliary agent selected from the group consisting of a wetting agent, a swelling agent, a penetrating agent, a solvent, a pH modifier, a surfactant, a perfume, and a thickener, and water.

11. A method for producing a dye for hair coloration represented by the following general formula (6), the method including performing a step 1 and a step 2:

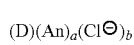 (6)

wherein in the formula (6), D represents a cationic moiety of the dye for hair coloration; An represents a polyatomic anion; and a and b each independently represent a value of 0 to 1, step 1: purifying a dye for hair coloration containing a polyatomic anion (An) with water and activated carbon; and step 2: dissolving the dye for hair coloration obtained in the step 1 with water and salt, and then subjected to salt exchange.

According to the step 1 and the step 2 performed, the dye for hair coloration represented by the general formula (6) has a proportion of the polyatomic ion (An) or impurities derived from An contained in the dye for hair coloration of 1% by mass or less.

Advantageous Effects of Invention

The dye for hair coloration of the present invention has a long shelf life and is excellent in heat resistance, and a composition for hair coloration that can effectively suppress decoloration of the dyed hair can be provided by using the dye for hair coloration. A dye for hair coloration that has a long shelf life and is excellent in heat resistance can be provided by the production method of the present invention.

DESCRIPTION OF EMBODIMENTS

Embodiments of the present invention will be described in detail below. The present invention is not limited to the following embodiments, and may be practiced with various modifications within the scope thereof.

The "dye for hair coloration" represented by the general formula (1) shows a water soluble dye formed of a compound that is used as a basic dye (or a cationic dye) for dyeing mainly human hair, and that has a group showing basicity (cationicity) in the molecular structure.

In the general formula (1), D represents a cationic moiety of the dye for hair coloration. The cation represented by D forms the dye for hair coloration through bonding to an anion. D preferably represents a monovalent cation.

In the general formula (1), An represents a polyatomic anion, and the dye for hair coloration of the present invention may contain the polyatomic anion (An) or "impurities derived from An" derived from the polyatomic anion (An), and is represented by the following general formula (1), in which the proportion (concentration ratio) of the "polyatomic anion (An) or impurities derived from An" in the entire of the dye for hair coloration is 1% by mass or less. The dye for hair coloration represented by the general formula (1) contains chloride ion (Cl⁻).

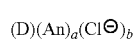
(1)

In the general formula (1), assuming that the molar ratio of D in the dye for hair coloration is 1, "a" represents the molar ratio of An, and "b" represents the molar ratio of Cl⁻. a and b each independently represent a value of 0 to 1, a preferably represents a value that is smaller than b, and a preferably represents 0 or a value close to 0. b preferably represents 1 or a value close to 1. For example, in the case where D represents a monovalent cation, and An represents a monovalent anion, a+b may be 1.

D preferably represents a monovalent cation, and in this case, a+b is preferably 1.

The product of the dye for hair coloration represented by the general formula (1) may contain impurities depending on the production process thereof and the storage condition after the production thereof. Examples of the impurities include an unreacted material in the synthesis, impurities attached to the raw materials, solvent molecules, an organic compound or an inorganic compound other than the target coloring component, an impurity derived from the cation or the anion (such as a decomposed product thereof, a substance in which the ion bonded to another substance, or the like), a hydrogen-containing compound containing proton (hydrogen ion) or the like (such as a reactive impurity containing an anion and a cation), an insoluble impurity, and a substance mixed therein before or after the production or in the production. In the present invention, the polyatomic anion (An) or a reaction product (product material) derived from the presence of An is designated as an impurity, which is unfavorable matter for the target function of hair coloration in the present invention (i.e., the heat resistance and the long term storage stability). Accordingly, the proportion (concentration ratio) of the "polyatomic anion (An) or impurities derived from An" in the entire of the dye for hair coloration is 0.1% by mass or less, and more preferably 0.05% by mass or less.

Examples of the "impurities derived from An" include a decomposition product of An, a substance in which An is bonded to another substance, such as the cationic moiety (D) of the dye for hair coloration, and a reaction product thereof.

In the general formula (1), the "polyatomic anion (An)" is specifically an anion having 2 or more atoms, and examples thereof include an inorganic anion, an organic anion, and a complex ion (complex anion). More specific examples thereof include dihydrogen phosphate ion ($H_2PO_4^-$), monohydrogen phosphate ion ($HPO_4^{2-}$), phosphate ion ($PO_4^{3-}$), $P_2O_7^{4-}$, cyanide ion ($CN^-$), nitrate ion ($NO_3^-$), nitrite ion ($NO_2^-$), hypochlorite ion ($ClO^-$), chlorite ion ($ClO_2^-$), chlorate ion ($ClO_3^-$), permanganate ion ($MnO_4^-$), carbonate ion ($CO_3^{2-}$), bicarbonate ion ($HCO_3^-$), hydrogen sulfate ion ($HSO_4^-$), sulfate ion ($SO_4^{2-}$), sulfite ion ($SO_3^{2-}$), thiosulfate ion ($S_2O_3^{2-}$), methyl sulfate ion ($CH_3SO_4^-$), hydrogen sulfide ion ($HS^-$), thiocyanate ion ($SCN^-$), tetrahydroxide aluminate ion ($[Al(OH)_4]^-$, $[Al(OH)_4(H_2O)_2]^-$), tetrahydroxide chromate (III) ion ($[Cr(OH)_4^-]$), chromate ion ($CrO_4^{2-}$), dichromate ion ($Cr_2O_7^{2-}$), tetrahydroxide zincate (II) ion ($[Zn(OH)_4]^{2-}$), tetracyanide zincate(II) ion ($[Zn(CN)_4]^{2-}$), ((1/2) $[ZnCl_2].Cl^-$), tetrachloride zincate(II) ion ($[ZnCl_4]^{2-}$), tetrachloride cuprate(II) ion ($[CuCl_4]^{2-}$), hexacyanide ferrate(III) ion ($[Fe(CN)_6]^{3-}$), hexacyanide ferrate(II) ion ($[Fe(CN)_6]^{4-}$), hexahydroxide stannate(IV) ion ($[Sn(OH)_6]^{2-}$), tetrahydroxide plumbate(II) ion ($[Pb(OH)_4]^{2-}$), acetate ion ($CH_3COO^-$), hydrogen oxalate ion ($H(COO)_2^-$), oxalate ion (($COO)_2^{2-}$), benzoate ion ($C_6H_5COO^-$), citrate ion ($C_6H_5O_7^{3-}$), various amino acid ions, and other organic acid ions having a carboxy group.

In the general formula (1), the polyatomic anion (An) is preferably a hydrogen-containing anion, and is specifically preferably $H_2PO_4^-$, $HCO_3^-$, $HSO_4^-$, $CH_3COO^-$, or $CH_3SO_4^-$.

In the dye for hair coloration represented by the general formula (1), while D and An each may be either a single component or a mixture of plural components, D is preferably a single component, and in general An is preferably a single component.

In the dye for hair coloration represented by the general formula (1), D may be a cationic moiety of a basic dye (cationic dye). In the general formula (1), D is specifically preferably a cationic moiety of an arylmethane dye, a triarylmethane dye, a xanthene dye, a phenothiazine dye, a phenazine dye, a phenoxazine dye, an azo dye, an azomethine dye, or an HC dye.

Specific examples of the dye for hair coloration of the present invention represented by the general formula (1) include an arylmethane dye, preferably a triarylmethane dye, such as C.I. Basic Blue 77 (wherein C.I. represents Color Index; the name may be referred simply to as Basic Blue 77 in the present invention, and the names of the following dyes are shown in this manner), Basic Blue 1, 5, 7, 11, 15, or 26, Basic Green 1 or 4, and Basic Violet 2, 3, 11:1, 4, or 14; a xanthene dye, such as Basic Violet 10 or 11, Basic Red 1 or 1:1, and rhodamine 110; a phenothiazine dye, such as Basic Blue 9 or 17; a phenazine dye, such as Basic Red 2; a phenoxazine dye, such as Basic Blue 3 or 124; an acridine dye; an azo dye, such as Basic Brown 16, Basic Red 22, 51, or 76, Basic Orange 31, and Basic Yellow 57; an azomethine dye, such as Basic Yellow 11, 13, 29, 36, or 40, and Basic Violet 16; and an HC dye, such as HC Blue 8, HC Red 13, and HC Yellow 9.

In the general formula (1), D is preferably represented by any one of the general formulae (2) to (5).

In the general formulae (2), (3), and (5), examples of the "halogen atom" represented by $R^1$ to $R^{21}$ and $R^{24}$ to $R^{26}$ include a fluorine atom, a chlorine atom, a bromine atom, and an iodine atom.

In the general formulae (2) to (5), examples of the "amino group having 0 to 20 carbon atoms, which may have a substituent" represented by $R^1$ to $R^{26}$ include $—NH_2$, a monosubstituted amino group, such as an ethylamino group, an acetylamino group, and a phenylamino group, and a disubstituted amino group, such as diethylamino group, a diphenylamino group, and an acetylphenylamino group. A quaternary ammonium group, which may have a substituent, formed of the amino group further having a substituent bonded thereto, such as a trialkylamino (or trialkylammonio) group, e.g., a trimethylamino (or trimethylammonio) group and a triethylamino (or triethylammonio) group, and a triphenylamino (or triphenylammonio) group, is also included in the "amino group having 0 to 20 carbon atoms, which may have a substituent", and these substituents may be the same as or different from each other.

In the general formulae (2) to (5), specific examples of the "linear or branched alkenyl group having 2 to 20 carbon atoms" in the "linear or branched alkenyl group having 2 to 20 carbon atoms, which may have a substituent" represented by $R^1$ to $R^{26}$ include a vinyl group, an allyl group, an isopropenyl group, a 2-butenyl group, a 1-hexenyl group, and a linear or branched group containing a plurality of these alkenyl groups bonded to each other.

In the general formulae (2), (3), and (5), specific examples of the "linear or branched alkyl group having 1 to 20 carbon atoms" in the "linear or branched alkyl group having 1 to 20 carbon atoms, which may have a substituent" represented by $R^1$ to $R^{21}$ and $R^{24}$ to $R^{26}$ include a linear alkyl group, such as a methyl group, an ethyl group, a n-propyl group, a butyl group, a pentyl group, a hexyl group, a heptyl group, an octyl group, a nonyl group, and a decyl group; and a branched alkyl group, such as an isopropyl group, an isobutyl group, a sec-butyl group, a tert-butyl group, an isooctyl group, and a tert-octyl group. The "linear or branched alkyl group having 1 to 20 carbon atoms" may form a ring to contain a cycloalkyl group having 3 to 20 carbon atoms, such as a cyclopropyl group, a cyclobutyl group, a cyclopentyl group, a cyclohexyl group, a cycloheptyl group, a cyclooctyl group, a cyclodecyl group, and a cyclododecyl group.

In the general formulae (2), (3), and (5), specific examples of the "linear or branched alkoxy group having 1 to 20 carbon atoms" in the "linear or branched alkoxy group having 1 to 20 carbon atoms, which may have a substituent" represented by $R^1$ to $R^{21}$ and $R^{24}$ to $R^{26}$ include a linear alkoxy group, such as a methoxy group, an ethoxy group, a propoxy group, a n-butoxy group, a n-pentyloxy group, a n-hexyloxy group, a heptyloxy group, an octyloxy group, a nonyloxy group, and a decyloxy group; and a branched alkoxy group, such as an isopropoxy group, an isobutoxy group, a sec-butoxy group, a tert-butoxy group, an isooctyloxy group, and a tert-octyloxy group. The "linear or branched alkoxy group having 1 to 20 carbon atoms" may form a ring to contain a cycloalkoxy group having 3 to 20 carbon atoms, such as a cyclopropoxy group, a cyclobutoxy group, a cyclopentyloxy group, and a cyclohexyloxy group.

In the general formulae (2), (3), and (5), specific examples of the "acyl group having 1 to 20 carbon atoms" in the "acyl group having 1 to 20 carbon atoms, which may have a substituent" represented by $R^1$ to $R^{21}$ and $R^{24}$ to $R^{26}$ include a formyl group, a carbonyl group, an acetyl group, a propionyl group, an acrylyl group, and a benzoyl group.

In the general formulae (2) to (5), specific examples of the "aromatic hydrocarbon group having 6 to 30 carbon atoms" in the "aromatic hydrocarbon group having 6 to 30 carbon atoms, which may have a substituent" represented by $R^1$ to $R^{26}$ include a phenyl group, a biphenylyl group, a terphenylyl group, a tetrakisphenyl group, a styryl group, a naphthyl group, an anthryl group, an acenaphthenyl group, a phenanthryl group, a fluorenyl group, an indenyl group, a pyrenyl group, and a triphenylenyl group. The "aromatic hydrocarbon group" in the present invention shows an aromatic hydrocarbon group and a condensed polycyclic aromatic group.

In the general formulae (2) to (5), specific examples of the "heterocyclic group having 2 to 30 carbon atoms" in the "heterocyclic group having 2 to 30 carbon atoms, which may have a substituent" represented by $R^1$ to $R^{26}$ include a triazinyl group, a pyridyl group, a pyrimidinyl group, an imidazolyl group, a furyl group, a pyrrolyl group, a thienyl group, a quinolyl group, an isoquinolyl group, a benzofuryl group, a benzothienyl group, a indolyl group, a carbazolyl group, a carbolynyl group, a pyridoindolyl group, an oxazolyl group, a benzoxazolyl group, a thiazolyl group, a benzothiazolyl group, a quinoxalyl group, a benzimidazolyl group, a pyrazolyl group, a dibenzofuryl group, a dibenzothienyl group, a naphthyridinyl group, a phenanthrolinyl group, an acrydinyl group, and a hydantoin group.

In the general formulae (2) to (5), specific examples of the "substituent" in the "amino group having 0 to 20 carbon atoms having a substituent", the "linear or branched alkenyl group having 2 to 20 carbon atoms having a substituent", the "linear or branched alkyl group having 1 to 20 carbon atoms having a substituent", the "linear or branched alkoxy group having 1 to 20 carbon atoms having a substituent", the "acyl group having 1 to 20 carbon atoms having a substituent", the "aromatic hydrocarbon group having 6 to 30 carbon atoms having a substituent", and the "heterocyclic group having 2 to 30 carbon atoms having a substituent" represented by $R^1$ to $R^{26}$ and the "amino group having 0 to 30 carbon atoms or the methylene group having a substituent" represented by Q include a nitro group ($-NO_2$), a nitroso group ($-NO$), a cyano group ($-CN$), a hydroxy group ($-OH$), a halogen atom, such as a fluorine atom, a chlorine atom, a bromine atom, and an iodine atom; an unsubstituted amino group; a monosubstituted or disubstituted amino group having a linear or branched alkyl group having 1 to 20 carbon atoms or an aromatic hydrocarbon group having 6 to 30 carbon atoms, such as a methylamino group, a dimethylamino group, a diethylamino group, an ethylmethylamino group, a methylpropylamino group, a di-tert-butylamino group, and a diphenylamino group; a sulfonamide group ($-S(=O)_2-NRR'$) (wherein "$-NRR'$" in the group represents a unsubstituted amino group; a monosubstituted or disubstituted amino group having a linear or branched alkyl group having 1 to 20 carbon atoms or an aromatic hydrocarbon group having 6 to 30 carbon atoms, such as a methylamino group, a dimethylamino group, a diethylamino group, an ethylmethylamino group, a methylpropylamino group, a di-tert-butylamino group, and a diphenylamino group); a linear or branched alkyl group having 1 to 20 carbon atoms, such as a methyl group, an ethyl group, a n-propyl group, an isopropyl group, a n-butyl group, a sec-butyl group, a tert-butyl group, a pentyl group, a n-hexyl group, an isohexyl group, a heptyl group, a n-octyl group, a tert-octyl group, an isooctyl group, a nonyl group, and a decyl group; a cycloalkyl group having 3 to 20 carbon atoms, such as a cyclopropyl group, a cyclobutyl group, a cyclopentyl group, a cyclohexyl group, a cycloheptyl group, a cyclooctyl group, a cyclodecyl group, and a cyclododecyl group; a linear or branched alkoxy group having 1 to 20 carbon atoms, such as a methoxy group, an ethoxy group, a propoxy group, a tert-butoxy group, a n-pentyloxy group, and a n-hexyloxy group; a cycloalkoxy group having 3 to 20 carbon atoms, such as a cyclopropoxy group, a cyclobutoxy group, a cyclopentyloxy group, and a cyclohexyloxy group; a linear or branched alkenyl group having 2 to 20 carbon atoms, such as a vinyl group, a 1-propenyl group, an allyl group, a 1-butenyl group, a 2-butenyl group, a 1-pentenyl group, a 1-hexenyl group, an isopropenyl group, an isobutenyl group, and a group containing a plurality of these alkenyl groups bonded to each other; an acyl group having 1 to 20 carbon atoms, such as a formyl group, an acetyl group, a propionyl group, an acrylyl group, and a benzoyl group; an aromatic hydrocarbon group having 6 to 30 carbon atoms, such as a phenyl group, a naphthyl group, an anthryl group, a phenanthryl group, a pyrenyl group, a triphenylenyl group, an indenyl group, a fluorenyl group, and a styryl group; heterocyclic group having 2 to 30 carbon atoms, such as a pyridyl group, a pyrimidinyl group, a triazinyl group, a pyrrolyl group, an imidazolyl group, a pyrazolyl group, a triazolyl group, a pyrazinyl group, a pyridazinyl group, a piperidinyl group, a piperadinyl group, a quinolyl group, an isoquinolyl group, a naphthyridinyl group, an indolyl group, a benzimidazolyl group, a carbazonyl group, a carbolynyl group, a pyridoindolyl group, an acridinyl group, a phenanthrolinyl group, a phenanthridinyl group, a hydantoin group, a furyl group, a benzofuryl group, a dibenzofuryl group, a pyranyl group, a coumarinyl group, an isobenzofuryl group, a xanthenyl group, an oxanthrenyl group, a pyranonyl group, a thienyl group, a thiopyranyl group, a benzothienyl group, a dibenzothienyl group, a thioxanthenyl group, an oxazolyl group, a benzoxazolyl group, a morpholinyl group, a thiazolyl group, and a benzothiazolyl group; and a cyclic olefin group having 3 to 30 carbon atoms, such as a cyclopropenyl group, a cyclobutenyl group, a cyclopentenyl group, a cyclohexenyl group, a cycloheptenyl group, a (1,3- or 1,4-)cyclohexadienyl group, and a 1,5-cyclooctadienyl group. For these "substituents", only one thereof may be contained, and a plurality thereof may be contained, and in the case where a plurality thereof is contained, the substituents may be the same as or different from each other. These "substituents" each may further have the substituent. In the case where the "substituent" contains a carbon atom, the carbon atom is counted in "0 to 20 carbon atoms", "2 to 20 carbon atoms", "1 to 20 carbon atoms", "6 to 30 carbon atoms", and "2 to 30 carbon atoms" in the general formulae (2) to (5). These substituents may be bonded to each other via a single bond, a substituted or unsubstituted methylene group, an oxygen atom, or a sulfur atom, so as to form a ring.

In the general formula (2), $R^1$ to $R^{13}$ each preferably represent —H, a halogen atom, an amino group having 0 to 20 carbon atoms, which may have a substituent, an alkenyl group having 2 to 20 carbon atoms, which may have a substituent, or a linear or branched alkyl group having 1 to 10 carbon atoms, which may have a substituent.

In the general formula (2), adjacent groups of $R^1$ to $R^{13}$ may be bonded to each other to form a ring, and in the case where a ring is formed, it is preferred that $R^3$ and $R^4$, $R^7$ and $R^8$, and $R^9$ to $R^{13}$ each are bonded to form a ring, and it is more preferred that the ring is a 5-membered ring or a 6-membered ring.

In the general formula (3), $R^{14}$ to $R^{21}$ each preferably represent —H, an amino group having 0 to 20 carbon atoms, which may have a substituent, or an aromatic hydrocarbon group having 6 to 30 carbon atoms, which may have a substituent.

In the general formula (3), adjacent groups of $R^{14}$ to $R^{21}$ may be bonded to each other to form a ring, and in the case where a ring is formed, it is preferred that $R^{14}$ to $R^{17}$ or $R^{18}$ to $R^{21}$ are bonded to form a ring, and it is more preferred that the ring is a 5-membered ring or a 6-membered ring.

In the general formula (4), $R^{22}$ and $R^{23}$ each preferably represent an aromatic hydrocarbon group having 6 to 30 carbon atoms, which may have a substituent, or a heterocyclic group having 2 to 30 carbon atoms, which may have a substituent.

In the general formula (5), $R^{24}$ to $R^{26}$ each preferably represent a linear or branched alkyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent.

In the general formula (5), $R^{25}$ and $R^{26}$ may be bonded to each other to form a ring, and in the case where a ring is formed, it is preferred that the ring is a 5-membered ring or a 6-membered ring.

Specific examples of the compound that is preferred as the dye for hair coloration of the present invention represented by the general formula (1) are shown below. The structural formulae shown as the examples are in the case where a is 0, and b is 1 in the general formula (1). The present invention is not limited to the compounds. In the following structural formulae, hydrogen atoms are partially omitted from the description, and even in the case where there are stereoisomers, only the planar structural formula is shown.

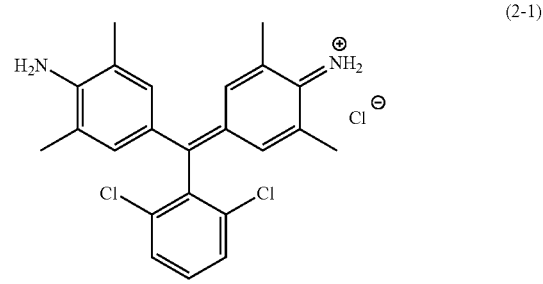

(2-1)

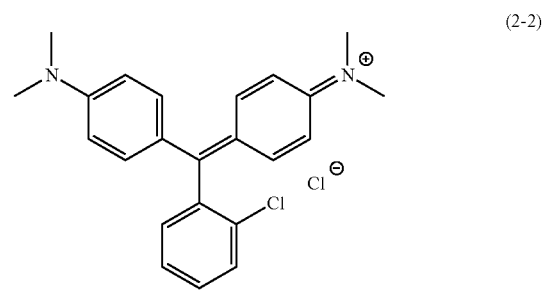

(2-2)

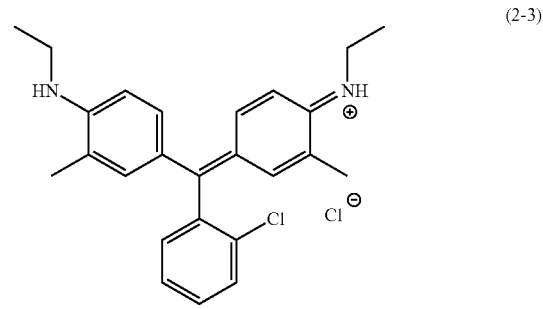

(2-3)

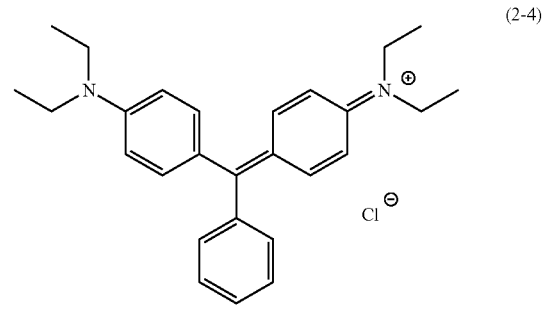

(2-4)

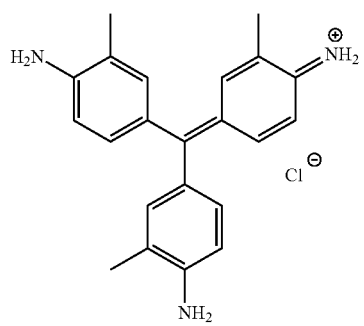
(2-5)
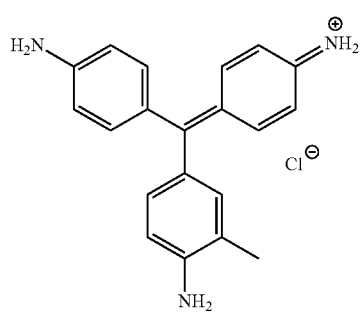
(2-6)
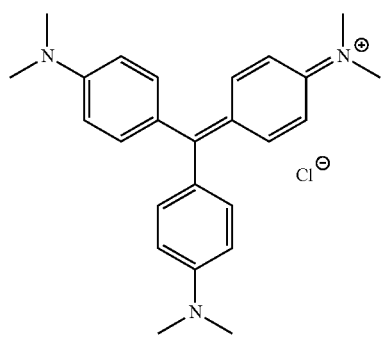
(2-7)
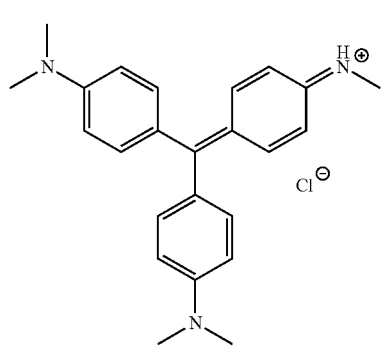
(2-8)
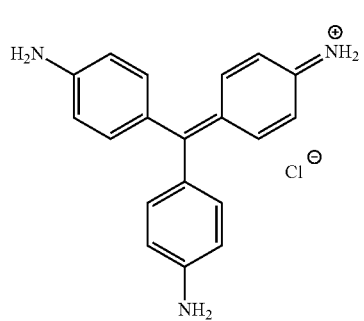
(2-9)
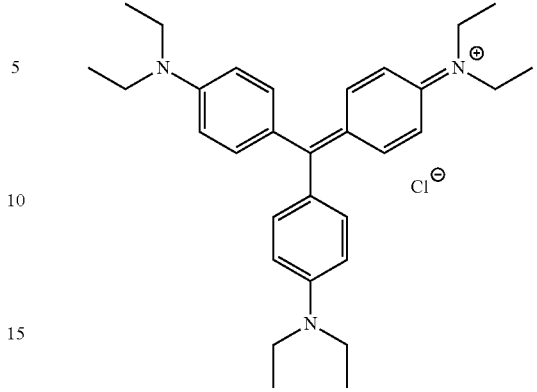
(2-10)
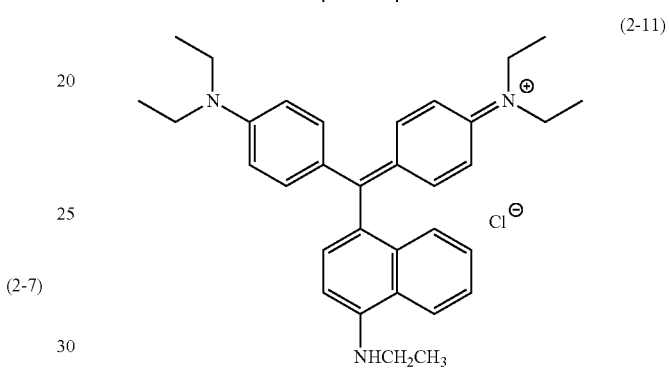
(2-11)
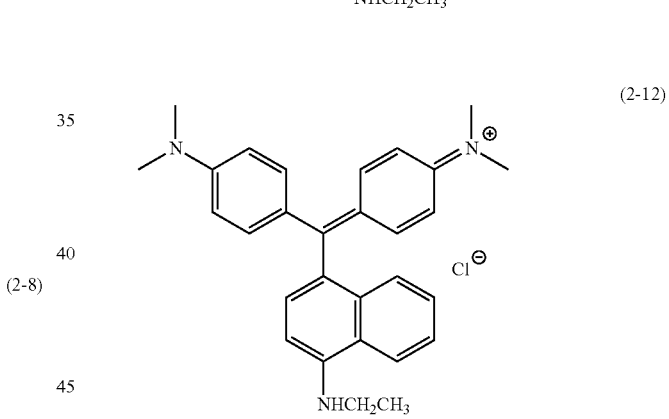
(2-12)
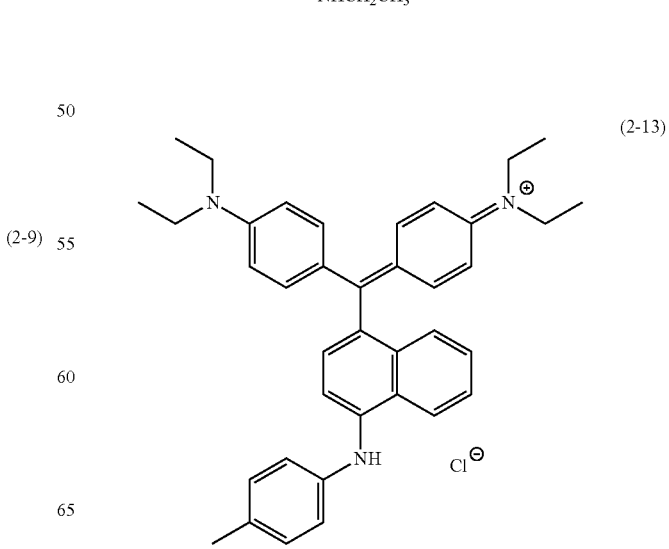
(2-13)

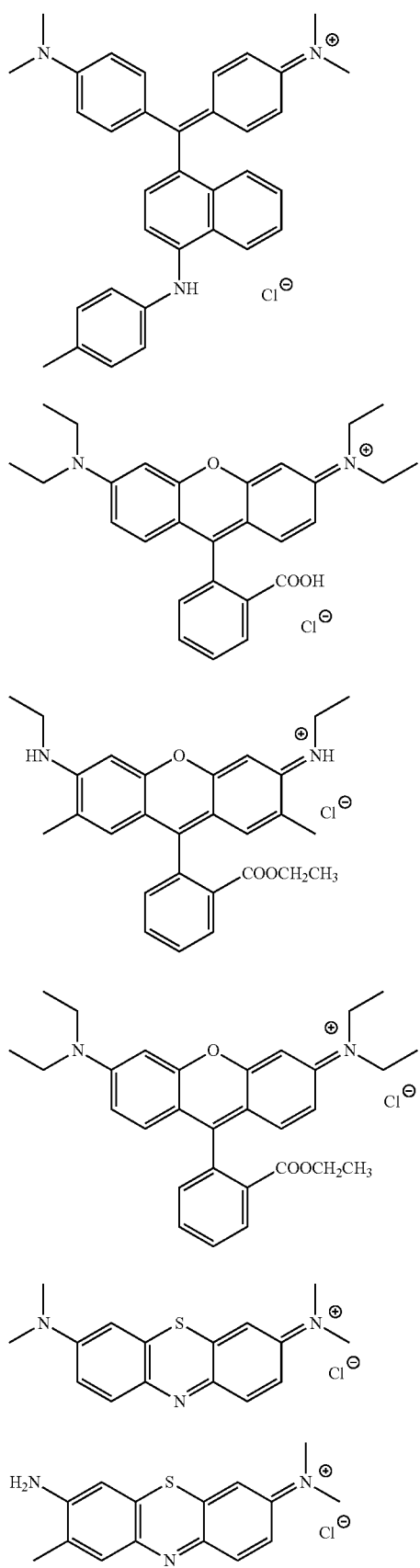
(2-14)
(A-1)
(A-2)
(A-3)
(B-1)
(B-2)
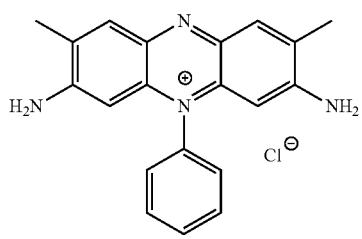
(C-1)
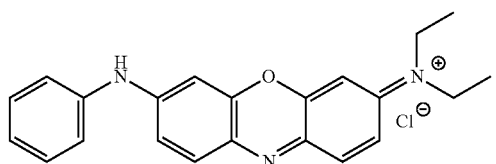
(D-1)
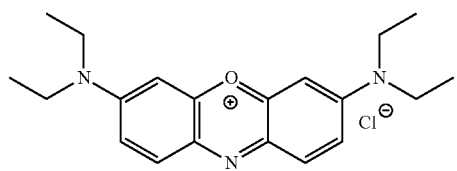
(D-2)
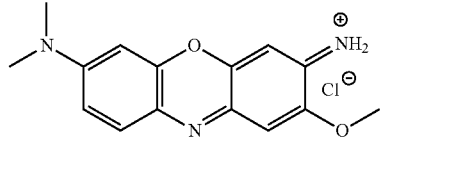
(D-3)
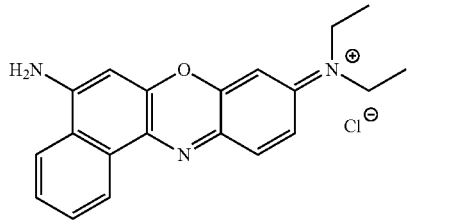
(D-4)
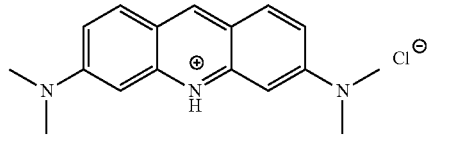
(E-1)
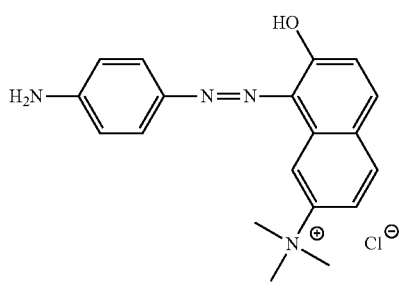
(F-1)

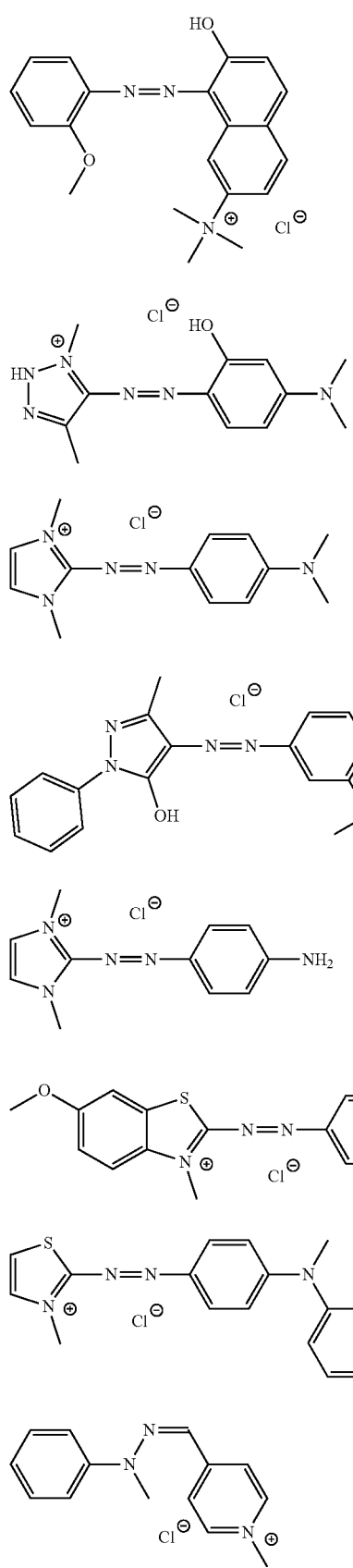
(F-2)
(F-3)
(F-4)
(F-5)
(F-6)
(F-7)
(F-8)
(G-1)
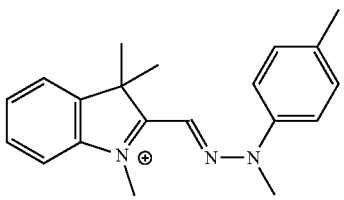
(G-2)
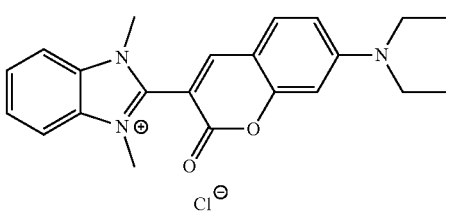
(G-3)
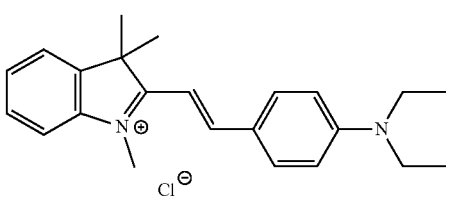
(G-4)
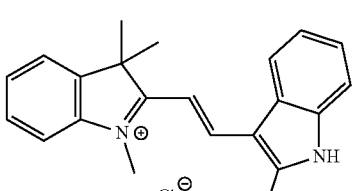
(G-5)
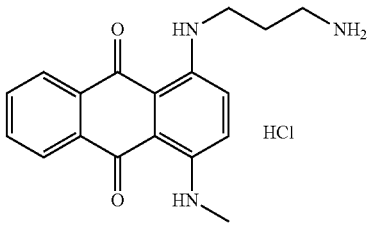
(H-1)
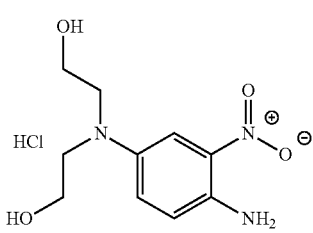
(H-2)
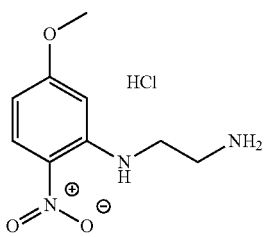
(H-3)
The specific examples of the dye for hair coloration of the present invention are shown above, and in the case where these dyes are actually used in a dye composition for hair coloration, it is preferred to select the dye that is free of toxicity and allergenic potency wherever possible, and to use the dye that has high safety.

The dye for hair coloration represented by the general formula (1) can be produced (synthesized) by using a commercially available dye (or a colorant, such as a pigment) as a starting material. The compound represented by the general formula (1) may also be produced by using a newly synthesized colorant compound as a starting material. An example of a method for producing the dye for hair coloration of the present invention will be described below. The dye used as a starting material is not particularly limited, and is preferably a basic dye having a cationic chromogenic part and an anionic nonchromogenic part. Examples of the starting material include a dye having a structure obtained by replacing the anionic moiety of the aforementioned specific example of the dye for hair coloration by an anion other than chloride ion. However, a dye containing chloride ion in a certain proportion in the raw material may be used.

The method for producing a dye for hair coloration of the present invention is a method for producing a dye for hair coloration represented by the following general formula (6). A dye represented by the similar general formula (6) may also be used as a starting material in the method for producing a dye for hair coloration of the present invention.

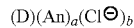
(6)

In the general formula (6), for example, D represents the cationic moiety of the target dye for hair coloration of the present invention; An represents a polyatomic anion, which may contain Cl$^-$; and a and b each independently represent a value of 0 to 1, provided that the magnitude relationship between a and b is not limited.

In the production method of the present invention, the basic dye (cationic dye) represented by the general formula (6) may be, for example, an arylmethane dye, a triarylmethane dye, a xanthene dye, a phenothiazine dye, a phenazine dye, a phenoxazine dye, an azo dye, an azomethine dye, or an HC dye, and may be a dye having D corresponding to the cationic moiety represented by the general formulae (2) to (5). A triarylmethane dye represented by the general formula (2) will be described herein as a specific example.

In the case where the dye for hair coloration of the present invention is a triarylmethane dye, it is preferred that in the general formula (2), $R^1$, $R^2$, $R^5$, and $R^6$ each represent —H or a methyl group, $R^3$, $R^4$, $R^7$, and $R^8$ each represent —H, a methyl group, or an ethyl group, and $R^9$ to $R^{13}$ each represent —H, —Cl, an amino group having 0 to 10 carbon atoms, which may have a substituent, an alkenyl group having 2 to 10 carbon atoms, which may have a substituent, an alkyl group having 1 to 10 carbon atoms, which may have a substituent, or an acyl group having 1 to 10 carbon atoms, which may have a substituent.

In the case where in the general formula (6), D represents a cationic moiety represented by the general formula (2), wherein $R^1$, $R^2$, $R^5$, and $R^6$ each represent a methyl group, $R^3$, $R^4$, $R^7$, $R^8$, and $R^{10}$ to $R^{12}$ each represent —H, and $R^9$ and $R^{13}$ each represent —Cl, a is 1, b is 0, and An represents $H_2PO_4^-$, the general formula (6) shows a dye for hair coloration represented by the following formula (2-1X) (HC dye, HC Blue 15, molecular weight: 495.34).

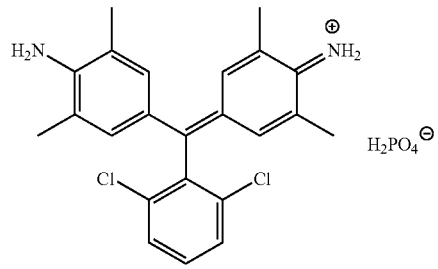
(2-1X)

The method for producing a dye for hair coloration of the present invention includes performing the step 1 and the step 2 shown below. An example will be shown in which the basic dye represented by the formula (2-1X) containing a polyatomic anion as a major anion other than chloride ion in the dye is used as a starting material in the method for producing a dye for coloration of the present invention.

Step 1: Purifying a dye for hair coloration containing a polyatomic anion (An) with water and activated carbon Step 2: Dissolving the dye for hair coloration obtained in the step 1 with water and salt, and then performing salt exchange In the step 1, the step of "purifying with water and activated carbon" may specifically include the following steps. The dye provided as the starting material is dissolved in water under suitable conditions including concentration, temperature, and agitation condition.

Subsequently, the solution is mixed with suitable activated carbon and purified therewith under suitable conditions including temperature and agitation condition. Thereafter, a purified specimen may be obtained through washing, filtration, and the like.

Subsequently, in the step 2, the step of "dissolving the dye for hair coloration obtained in the step 1 with water and salt, and then performing salt exchange" may specifically include the following steps. The specimen obtained through purification in the step 1 is mixed with water and salt (NaCl) and treated under suitable conditions including salt concentration, temperature, and agitation condition, so as to provide the target dye for hair coloration through salting out. According to the procedure, the dye for hair coloration represented by the general formula (6) can be obtained, in which a part, the most portion, or the entire of the polyatomic anion contained in the dye before the steps 1 and 2 is replaced by chloride ion (salt exchange). Filtration, washing, drying, and the like may be appropriately performed during the operation of the step 2 or before or after the operation.

By performing the step 1 and the step 2 as described above, the dye for hair coloration represented by the general formula (6) that has a proportion of the polyatomic ion (An) or impurities derived from An contained of 1'. by mass or less can be obtained.

The step 1 and the step 2 of the production method will be described in detail below. The "water" used is not particularly limited, and ordinary water may be used, examples of which include tap water, deionized water, distilled water, and industrial water. The concentration of the other components than the cation and anion contained in the target dye is preferably small wherever possible, as far as the advantageous effects of the present invention are not impaired. The water in the present invention may be public water, such as tap water.

In the step 1, the mixing ratio when the dye for hair coloration and water are mixed is not particularly limited, as far as the dye can be sufficiently dissolved at that concentration. Specifically, the mass of water used may be 5 to 1,000 times, and more preferably 10 to 100 times, the mass of the dye.

The vessel used in the step 1 and the step 2 is not particularly limited, as far as the vessel is for ordinary synthesis, purification, mixing, and agitation. The material of the vessel used may be selected from suitable materials, for example, a glass vessel, such as a flask, a metal vessel, a resin vessel, a glass-lined vessel. A vessel formed of a material that withstands the use of water and salt (NaCl) is preferably used. The agitation device used may be a commercially available product, and the shape of the agitation blade and the kind of the agitator are not particularly limited.

The temperature in agitating the dye and water in the step 1 is preferably room temperature (around 20 to 25° C.) to 100° C., and more preferably 40 to 80° C. The period of time of agitation required for dissolving is not particularly limited, as far as the dye is sufficiently dissolved, and is preferably 30 minutes to 12 hours, and more preferably 30 minutes to 3 hours. The temperature suitable for the agitation and the agitation time depends on the kind of the dye and the mass of the dye to be dissolved, and thus the dye is preferably dissolved at a temperature and in an agitation time suitable therefor.

The purification in the production method of the present invention may be performed, for example, by a known method, such as purification by column chromatography; adsorption purification with silica gel, activated carbon, activated clay, or the like; and recrystallization or crystallization with a solvent, and it is preferred to use activated carbon as in the step 1. The aforementioned purification methods may be performed before and after the use of activated carbon, and only activated carbon may be used. In the purification in the present invention, it is preferred to use only activated carbon.

In the step 1, the activated carbon used may be various commercially available products used for water clarification, decoloration, and purification of chemical compounds, and is not particularly limited. Examples of the shape of the activated carbon particles include a powder form, a granular form, a bar form, and a fibrous form, and activated carbon in a powder form is preferred. The pore diameter on the surface of the activated carbon may be, for example, 2 to 3 nm. The properties of the activated carbon may be appropriately selected depending on the kinds of the cation and the anion contained in the raw materials.

In the step 1, it is preferred that the activated carbon is added to the solution having the dye sufficiently dissolved therein, and then mixed and agitated. The amount of the activated carbon used is preferably not excessive with respect to the mass of the dye as a raw material, and is more preferably 1 to 100% by mass, and further preferably 5 to 30% by mass, based on the mass of the dye. As for the conditions in mixing the activated carbon in the solution, the agitation conditions, such as the temperature and the agitation time, may be the similar conditions as in dissolving the dye initially.

In the step 1, after performing the treatment using the activated carbon, filtration and washing of the activated carbon are performed with water. During the filtration and washing, the resulting aqueous solution of the dye may be at room temperature or heated, and the aqueous solution is preferably heated to a temperature in a certain range. The aqueous solution of the dye thus purified in the step 1 is transferred to the step 2.

The aqueous solution of the dye for hair coloration obtained in the step 1 is supplied to the step 2. Salt (NaCl) is added to the aqueous solution of the dye for hair coloration dissolved therein under agitation at a temperature of 20 to 80° C., followed by agitation. The temperature in agitation may be a suitable temperature within a range of 20 to 80° C., and is preferably 30 to 70° C., and more preferably 40 to 65° C. The salt added is not particularly limited, and preferably has a less amount of impurities, and either an edible product or an industrial product may be used. The particle shape thereof is not particularly limited, and any form of a powder form, a pulverized form, and a granulated form may be used. The water content thereof may be any quality that is generally applied to business use, industrial use, or edible use. The salt concentration may be 1.5 to 25% by mass, and preferably 5 to 20% by mass, based on the solvent (water). The salt may be added in the form of an aqueous solution using water to the solution.

In the step 2, the liquid obtained by dissolving the salt in the aqueous solution containing the dye for hair coloration is heated to a suitable temperature for a certain period of time. The heating time may be appropriately selected from 1 to 24 hours. After heating, the liquid may be cooled to room temperature at a suitable cooling rate. During cooling to room temperature, the liquid is preferably agitated for a sufficiently long period of time, for example, approximately 5 to 24 hours. During the process of adding the salt and cooling under agitation, the reaction (salt exchange) of exchanging a part or the entire of the anion in the dye before the step 1 to chloride ion ($Cl^-$) occurs, and the dye for hair coloration represented by the general formula (1) can be obtained as an undissolved component in the aqueous solution, i.e., a precipitated solid matter.

The dye for hair coloration of the present invention obtained through dissolution with water and the salt and salt exchange as in the step 2, i.e., the solid matter precipitated through salt exchange, may be filtered and washed with an aqueous solution containing salt (salt water).

The salt concentration in the salt water is preferably 1.5 to 20% by mass. The temperature in filtration may be appropriately selected from room temperature to 40° C. After the filtration, the resulting composition containing the dye for hair coloration of the present invention and water (which may be, for example, in the form of solid, powder, or cake) has a certain water content. The composition may be dehydrated with a suction filter or the like.

For the composition containing the dye for hair coloration of the present invention and water obtained in the step 2, water (or the water content) in the composition containing the dye for hair coloration may be controlled or eliminated with a suitable dryer. The composition may be dried for providing the composition for hair coloration of the present invention by transferring to a vessel having a large base area, such as a dish or a tray. The composition may be dried with a hot air dryer or a vacuum dryer. The drying time may be a suitable period of time for providing the target water content, and may be selected from 1 hour to 3 days. The water content in the composition containing the dye for hair coloration is preferably 10% by mass or less, and more preferably 8% by mass or less. The composition may be dried substantially completely to 1% by mass or less, or water may remain to a certain extent. The temperature in drying is preferably in a range of 20 to 100° C., and more preferably 30 to 80° C.

The dye for hair coloration of the present invention is obtained by the method including the step 1 and the step 2 described above, and modified known steps may be added before or after the steps.

The dye for hair coloration of the present invention represented by the general formula (1) may be subjected to ultraviolet visible spectral analysis (UV-Vis) or absorbance analysis, thermogravimetric differential thermal analysis (TG-DTA), high pressure liquid chromatography (HPLC), gas chromatography (GC), nuclear magnetic resonance (NMR), and the like, for the identification and the property evaluation analysis of the compound. In the absorbance analysis and the HPLC measurement, comparison based on the molecular structure and the color can be performed, and thus the purity of the target dye for hair coloration in the specimen and the impurity concentration in the specimen can be evaluated.

For example, the purity or the concentration ratio of the major component can be measured in such a manner that the HPLC measurement is performed at particular measurement wavelengths to provide peak areas of peaks measured at retention times, from which the ratios (area ratios) of the major component and the impurity are determined.

The dye for hair coloration of the present invention represented by the general formula (1) is obtained through the aforementioned steps. Due to the purification, the concentration of the component that is not water soluble, i.e., the insoluble component, in the dye for hair coloration can be decreased to 1% by mass or less, more preferably 0.5% by mass or less, and further preferably 0.1, by mass or less. As one of the characteristic features of the method for producing a dye for hair coloration of the present invention, the concentration of the anion contained before the steps of purification and salt exchange can be reduced, and thus the alteration and deterioration of the quality caused by the anion contained in the dye for hair coloration before the steps can be prevented.

The mechanism of the prevention of the alteration and deterioration of the quality of the dye for hair coloration of the present invention represented by the general formula (1) specifically includes the advantage that the major component of the anion after the steps is chloride ion, and thus the anion is not decomposed by itself. In other words, the possibility of the occurrence of the alteration due to decomposition of the polyatomic ion contained in the dye before the steps, the alteration due to reaction of the polyatomic ion and the dye (chromogenic part), and the alteration due to reaction with water molecules or the component in the dye composition for hair coloration can be reduced. In the case where the polyatomic anion is a hydrogen-containing anion, in particular, it is considered that a hydrogen ion released from the ion influences the decomposition of the dye molecule and the other components. It is considered that the reaction of the aforementioned alteration and decomposition of the component proceeds not only around room temperature, but in the case where the temperature is higher than the room temperature, and, in particular, the reaction of the decomposition and alteration is accelerated at a temperature, at which the composition for hair coloration is used, particularly 35° C. or more.

The shelf life of the dye for hair coloration of the present invention and the extent of alteration of the dye for hair coloration can be measured by the HPLC measurement, absorbance analysis, or the like. Specifically, the purity of the dye for hair coloration at the start of evaluation as the standard is preferably 99% or more. The purity is preferably retained to 99, or more for a period of certain days or longer through time-dependent change. The temperature for measuring the time dependent change may be room temperature, room temperature or more, preferably 40° C. or more, and more preferably 40 to 60° C. The period of time where the purity is retained is preferably 6 months or more at room temperature. The shelf life is preferably 6 months or more at a room temperature (20 to 25° C.) or 7 days or more at a room temperature of 40 to 60° C.

The chromatic characteristics (such as the color valency and the hue) of the dye for hair coloration of the present invention may be evaluated by measuring the absorbance, the visible light absorption spectrum or reflection spectrum, for example, in a range of 400 to 700 nm, the chromaticity coordinate (x, y) in the xy chromaticity diagram of the CIE 1931 color system using a spectrocolorimeter or a color difference meter, the density (K/Sd), the color tone (L*, a*, b*) of the CIE 1976 color system, the color difference ($\Delta E^*$), and the like, in the state of powder (solid), a solution, a dispersion, or a thin film. There are cases where solutions, powders, or thin films of compounds having the same molecular structure have different visual colors, and for objectively quantifying the color difference, the measurement with a spectrocolorimeter or a color difference meter may be performed. The visual evaluation with standard color samples, a color chart, or the like may also be performed. The color tone obtained by actually dyeing fibers, such as a white hair specimen, may be evaluated.

The dye for hair coloration of the present invention retains the structure of the dye molecule derived from the chromogenic part since the purification and salt exchange are performed before and after the steps, and the chromatic characteristics thereof are not impaired. The absorbance before the purification is preferably 0.5 or more.

According to the method for producing a dye for hair coloration and the evaluation method for a dye for hair coloration, the dye for hair coloration of the present invention having a long shelf life excellent in heat resistance can be obtained.

The dye for hair coloration according to the present invention, the compound represented by the general formula (1), and the composition for hair coloration containing the dye for hair coloration are preferably used in the form of a so-called hair colorant. The dye for hair coloration represented by the general formula (1) may be used after mixing with such a component as another dye, an additive, and an auxiliary agent. An embodiment that is suitable for the dye for hair coloration of the present invention is a composition for hair coloration, which may contain a dye for hair coloration containing the compound represented by the general formula (1), at least one kind of an auxiliary agent selected from the group consisting of a wetting agent, a swelling agent, a penetrating agent, a solvent, a pH modifier, a surfactant, a perfume, and a thickener, and water.

Examples of the wetting agent include glycerin, propylene glycol, a sorbitol compound, 1,3-butylene glycol, and a polyethylene glycol compound. In the case where the wetting agent is used, the content thereof is preferably 0.1 to 20% by mass, and more preferably 0.5 to 10% by mass, based on the total amount of the composition for hair coloration.

Examples of the swelling agent include an alkali aqueous solution containing ammonia (ammonium hydroxide) or monoethanolamine (MEA). In the case where the swelling agent is used, the content thereof is preferably 0.1 to 20% by mass, and more preferably 0.5 to 10% by mass, based on the total amount of the composition for hair coloration.

Examples of the penetrating agent and the solvent include a monohydric alcohol having an alkyl group having 1 to 6 carbon atoms, such as ethanol, 1-propanol, 2-propanol, 1-butanol, 2-butanol, and butoxyethanol; a polyhydric alcohol having 3 to 8 carbon atoms or an ether thereof, such as propanediol, butanediol, pentanediol, hexanediol, hexanetriol, heptanediol, heptanetriol, octanediol, octanetriol, isoprene glycol, propylene glycol, glycerin, and diethylene glycol monoethyl ether; an N-alkylpyrrolidone that is in a liquid state at room temperature (around 25° C.), such as N-methyl-2-pyrrolidone, N-ethyl-2-pyrrolidone, N-propyl-2-pyrrolidone, N-butyl-2-pyrrolidone, and N-cyclohexyl-2-pyrrolidone; an alkylene carbonate (lower alkylene carbonate), such as ethylene carbonate and propylene carbonate; and an aromatic alcohol, such as benzyloxyethoxyethanol, benzyl alcohol, benzyloxyethanol, cinnamyl alcohol, p-anisyl alcohol, p-methylbenzyl alcohol, phenoxyethanol, phenoxyisopropanol, 2-benzylethanol, and g-phenylethyl alcohol. Among these, an aromatic alcohol and an N-alkylpyrrolidone are preferred, and benzyl alcohol, benzyloxyethoxyethanol, and benzyloxyethanol are more preferred. In the case where the penetrating agent or the solvent is used, the content thereof is preferably 2 to 40% by mass, and more preferably 5 to 20% by mass, based on the total amount of the composition for hair coloration.

Examples of the pH modifier include an acid, such as phosphoric acid, lactic acid-sodium lactate, and citric acid-sodium citrate, and a base, such as aqueous ammonia, sodium hydroxide, potassium hydroxide, and sodium carbonate. In the case where the pH modifier is used, the content thereof is preferably 0.1 to 10% by mass, and more preferably 0.5 to 5% by mass, based on the total amount of the composition for hair coloration.

As the surfactant, a cationic surfactant or a nonionic surfactant is mainly used. Specific examples thereof include a silicone compound, such as polysiloxane, a polyoxyethylene alkyl ether, a polyoxyethylene fatty acid ester, a polyglycerin fatty acid ester, an aliphatic amine or a quaternary ammonium salt thereof (such as trimethylstearylammonium chloride), a sugar alcohol ether compound, such as a sorbitol alkyl ether, and a polyoxyethylene sorbitan fatty acid ester, but are not limited to these compounds. Among these, a polyoxyethylene sorbitan fatty acid ester is preferred. The use of a polyoxyethylene sorbitan fatty acid ester further enhances the contamination reduction effect to the skin (skin contamination preventing capability).

The polyoxyethylene sorbitan fatty acid ester used is preferably at least one kind selected from the group consisting of polyoxyethylene sorbitan monolaurate, polyoxyethylene sorbitan monopalmitate, polyoxyethylene sorbitan monostearate, and polyoxyethylene sorbitan monooleate.

In the case where the surfactant is used, the content thereof is preferably 0.1 to 20% by mass, and more preferably 0.5 to 10% by mass, based on the total amount of the composition for hair coloration from the standpoint of the reduction of the contamination to the skin.

Examples of the perfume include vanillin, cinnamic alcohol, heliotropin, coumarin, 2-methyl-3-(3,4-methylenedioxyphenyl)propanal, 4-(4-hydroxyphenyl)-2-butanone, benzaldehyde, anisyl alcohol, 3,4-dimethoxybenzaldehyde, heliotropyl acetate, phenylacetaldehyde dimethyl acetal, phenoxyethyl alcohol, phenylacetaldehyde glyceryl acetal, furaneol, sugar lactone, maltol, ethylmaltol, ethyl diglycollate, benzyl acetate, linalool, camphor, terpineol, citronellol, geraniol, 2,6-nonadienal, methyloctyl carbonate, 3,7-dimethyl-2,6-octadienal, and nonanal. In the case where the perfume is used, the content thereof is preferably 0.00001 to 2% by mass based on the total amount of the composition for hair coloration.

Examples of the thickener include thickeners derived from guar gum and a derivative thereof, hydroxyethyl cellulose, xanthan gum, collagen, gelatin, carboxymethyl cellulose sodium salt, Carbopol (trade name), sodium alginate, gum arabic, a cellulose derivative, and poly (ethylene oxide). The thickener has an effect of increasing the viscosity of the composition for hair coloration to make a gel-like form, which is readily handled. In the case where the thickener is used, the content thereof is preferably 0.1 to 20% by mass, and more preferably 0.5 to 10% by mass, based on the total amount of the composition for hair coloration.

Water used in the composition for hair coloration is not particularly limited, and ion exchanged water, purified water, clean water, tap water, and the like may be used.

The dye for hair coloration represented by the general formula (1) of the present invention is excellent by itself in hair dyeing power and robustness as a dye for hair coloration, and can dye hair uniformly. The color thereof can be regulated to various colors (such as violet, green, brown, and black) by combining a dye for hair coloration containing the compound represented by the general formula (1) and a dye for hair coloration of another color.

Examples of the basic dye to be combined include a direct dye having an amino group or a substituted amino group in the molecule, and specific examples thereof include Red No. 213 (C.I. Basic Violet 10, rhodamine B), Red No. 214 (C.I. Basic Violet, rhodamine B acetate); Basic Blue (C.I. Basic Blue) 7, 9, 26, 75, or 99; Basic Red (C.I. Basic Red) 2, 22, 51, or 76; Basic Yellow (C.I. Basic Yellow) 57 or 87; Basic Orange (C.I. Basic Orange) 31; Basic Brown (C.I. Basic Brown) 16 or 17; and Basic Violet (C.I. Basic Violet) 2, 3, 4, or 14.

Examples of the HC dye to be combined include a direct dye having a nitro group in the molecule, and specific examples thereof include C.I. HC Blue 2 or 15; C.I. HC Red 1, 3, 7, 11, or 13; C.I. HC Yellow 2, 4, 5, 9, 11, or 13, C.I. HC Orange 1 or 2; C.I. HC Violet 1 or 2; and 4-hydroxypropylamino-3-nitrophenol.

The composition for hair coloration of the present invention in one embodiment preferably contains the dye for hair coloration represented by the general formula (1) in an amount of 0.001 to 5, by mass based on the total amount of the composition for hair coloration, with the balance containing at least one kind of an auxiliary agent selected from the group consisting of a wetting agent, a swelling agent, a penetrating agent, a solvent, a pH modifier, a surfactant, a perfume, and a thickener, and water. In the case where the content of the dye for hair coloration is less than 0.001% by mass, the effect of retaining the color tone and uniformly dyeing may be difficult to achieve, and in the case where an amount exceeding 5% by mass thereof is added, the enhancement of the effect of dyeing and the like may be small. The content of the dye for hair coloration is preferably 0.01 to 5% by mass, and more preferably 0.05 to 2% by mass, based on the total amount of the composition for hair coloration.

The pH value of the composition for hair coloration of the present invention is preferably 4 to 9, and more preferably 5 to 7. The pH value of the composition for hair coloration can be controlled by a known method, and is preferably controlled by using a pH modifier, such as citric acid monohydrate or trisodium citrate dihydrate. Specifically, in the case where the composition for hair coloration of pH 6 is to be produced, citric acid monohydrate and trisodium citrate dihydrate are dissolved in water to prepare an aqueous solution of pH 6 in advance, and then the dye for hair coloration containing the compound represented by the general formula (1) and depending on necessity the other additives (such as the auxiliary agent) are added to the aqueous solution to provide the composition for hair coloration of pH 6.

The composition for hair coloration of the present invention may further contain a known cosmetic component in such a range that does not impair the effects of the present invention. Examples of the cosmetic component capable of being added include a higher alcohol, Vaseline, a polyhydric alcohol, an ester compound, an antiseptic, a bactericide, a silicone derivative, and a water soluble polymer.

The hair dyeing method using the composition for hair coloration of the present invention may be specifically such a method that an object to be dyed, such as human hair or livestock hair, is made into contact with the composition for hair coloration of the present invention. The hair dyeing temperature is preferably 5 to 60° C., and in consideration that the operation is performed near the scalp skin, is more preferably 15 to 45° C. The hair dyeing time is preferably 5 to 60 minutes, and more preferably 10 to 30 minutes.

After the hair dying, an aftertreatment, such as water washing and drying, is generally performed. The water washing may be performed until the color of the hair colorant is no longer eluted at all, and may be performed, for example, by rinsing with flowing water at 5 to 40° C. and 5 to 15 L/min for 0.5 to 2 minutes. The drying after the water washing may be natural drying (generally at 5 to 40° C. for 10 minutes to 10 hours), and a hot air dryer (generally at 40 to 60° C. for 10 minutes to 10 hours) may be used depending on necessity.

After the water washing, soaping may be performed. The soaping may be performed, for example, by washing generally at a temperature of 15 to 50° C. for 1 to 10 minutes with an appropriate amount of a soaping liquid (which may be a mixed liquid of shampoo and warm water), and then washing with water until the soaping liquid is completely removed.

The resulting test specimen may be evaluated with a spectrocolorimeter. The hair dyeing density (K/Sd) may be evaluated in the following procedure. Specifically, it is possible that the test specimens before hair coloration (white hair) and after hair coloration (dyed hair) are measured for the reflectance (RA) at a wavelength (A) with a spectrocolorimeter, and the optical density (K/S) is calculated by the following Kubelka-Munk expression. The hair dyeing density $(K/S_d)$ can be obtained by subtracting the optical density (K/S) of the white hair from the optical density (K/S) of the dyed hair.

Kubelka-Munk expression:

$$K/S=\Sigma(1-R_\lambda)^2/2R_\lambda$$

$R_\lambda$: reflectance at wavelength ($\lambda$)
$\lambda$: 400 to 700 nm (interval: 10 nm)

The color tone of the resulting test specimen after hair coloration may be evaluated by measuring the color tone (L*, a*, b*) with the CIE L*a*b* color system. L* is the brightness, and a larger value thereof means a smaller intensity of coloration. a* and b* are the chromaticity showing the hue and the saturation. a* corresponds to the red/green axis, a positive value thereof is directed to red, and a negative value thereof is directed to green. b* corresponds to the yellow/blue axis, a positive value thereof is directed to yellow, and a negative value thereof is directed to blue.

The difference in color tone of different specimens can be calculated as the color difference $\Delta E^*$ and the hue difference $\Delta H^*$ from the values of $\Delta L^*$, $\Delta a^*$, and $\Delta b^*$ according to the following expression.

$$\Delta E^*=\{(\Delta L^*)^2+(\Delta a^*)^2+(\Delta b^*)^2\}^{1/2}$$

$$\Delta H^*=\{(\Delta a^*)^2+(\Delta b^*)^2\}^{1/2}$$

The extent of the change of the dyeing state (such as the presence of decoloration and the retention of clear color) can be evaluated by measuring $\Delta E^*$ or $\Delta H^*$ before and after various tests of the test specimen, such as the long-term storage test, the heat resistance test under heating, and the perspiration resistance test with an acidic or basic perspiration component. The dye for hair coloration of the present invention preferably has a smaller value of $\Delta E^*$ or $\Delta H^*$ obtained before and after the tests.

According to the embodiment described above, a composition for hair coloration that has a long shelf life and is excellent in heat resistance can be produced by using the dye for hair coloration according to the present invention. The composition for hair coloration of the present invention can exert an excellent dyeing effect in any of a hair coloring material, a hair coloring manicure, and a hair coloring treatment.

EXAMPLES

Embodiments of the present invention will be specifically described with reference to examples below, but the present invention is not limited to the examples.

Example 1

<Production of Dye for Hair Coloration "AHC Blue 77" Through Purification and Salt Exchange>

200 g of a commercially available blue dye (product name: HC Blue 15, available from CHROMEX) and 5.2 L of water were placed in a 10 L stainless steel vessel and dissolved by heating to 70° C. and agitating for 1 hour. 40 g of activated carbon (product name: Carboraffin, type: wet type, available from Osaka Gas Chemicals Co., Ltd.) was added to the solution, which was the agitated at 65° C. for 2 hours. After the agitation, the mixture was filtered at a hot state, and the filtered product was washed with 400 mL of water. The resulting filtrate was heated to 55° C., to which 275 g of edible salt was added, and the mixture was agitated for 1 hour, and gradually cooled to room temperature (25° C.) under agitation overnight. After the agitation, the deposit was filtered, and the resulting solid matter was washed with 200 mL of a saline solution of 2% by mass. The solid matter was dried in a hot air dryer (Forced Air Flow Oven (Windy Oven) WFO-601SD, available from EYELA Co., Ltd.) at 40° C. for 3 days, so as to provide "AHC Blue 77" as a blue solid matter (powder) (140 g, yield: 80.2%).

<Storage Stability Test of "AHC Blue 77">

The resulting solid matter (AHC Blue 77) was subjected to high pressure liquid chromatography (HPLC) measurement under the following measurement condition.

HPLC equipment: LC-20A (available from Shimadzu Corporation)
Eluent: (ammonium acetate/acetonitrile/water=1.5/0.5/98)/acetonitrile=1/1 (mass ratio), isocratic
Flow rate: 0.8 mL/min
Measurement wavelength: 254 nm
Column: L-column ODS (column diameter: 4.6 mm×length: 150 mm, particle diameter: 5 µm, pore diameter: 12 nm, available from General Incorporated Foundation, Chemicals Evaluation and Research Institute, Japan)

Column temperature: 40° C.

Preparation of specimen solution for measurement: 10 mg of the resulting solid specimen was dissolved in 2 mL of a mixed solvent of acetonitrile and water (2/3 (volume ratio)), and filtered with a syringe filter to prepare a solution, or an appropriate amount of the filtrate in the aforementioned process was dissolved in a mixed solvent of acetonitrile and water (2/3 (volume ratio)) to prepare a solution.

Injection amount of specimen solution: 1.0 μL

The dye for hair coloration (AHC Blue 77) represented by the following formula (2-1) was identified by HPLC measurement, and the HPLC purity thereof was 99.0 to 99.5%. The ion chromatography measurement (ion analyzer IA-300, available from DKK-TOA Corporation) thereof confirmed that the anion was Cl$^-$, and no other anion was detected. The target blue dye was measured as an HPLC measurement component at a peak of a retention time of 5.1 minutes. A reddish impurity at a retention time of 30.6 minutes could be detected, as one of purities, but the content thereof was less than the detection limit (which was designated as 0.01).

The results are shown in Table 1 as the purity (concentration ratio) (1) at the start of the storage stability test.

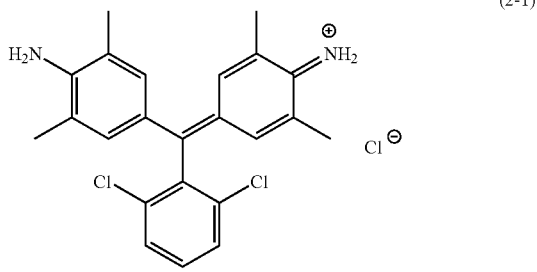

(2-1)

(Storage Stability Test Under Room Temperature Condition (Room Temperature Test))

The resulting solid matter (powder) specimen was placed in a transparent resin bottle, and allowed to stand in a laboratory room with common luminance at room temperature (approximately 25° C.) for 6 months. The powder specimen after allowing to stand for 6 months was measured for the purities (concentration ratios) (%) of the dye and the reddish impurity under the same HPLC measurement condition as above. The results of the room temperature test (6 months) are shown in Table 1.

(Storage Stability Test Under Heating Condition (Heating Test))

The solid powder specimen placed in a resin bottle as similar to the storage stability test at room temperature described above was heated to 60° C. for 7 days. The powder specimen after heating for 7 days was measured for the purities (concentration ratios) (%) of the dye and the reddish impurity under the same HPLC condition as above. The results of the heating test (7 days) are shown in Table 1.

Comparative Example 1

The blue dye represented by the formula (2-1X) was purified by a purification method different from the production method of the present invention. Specifically, 120 g of a commercially available blue dye (product name: HC Blue 15, available from CHROMEX) and 3 L of water were placed in a 5 L vessel and dissolved by agitating at 70° C. Subsequently, 24 g of the same activated carbon (Carboraffin) as used in Example 1 was added thereto, and the mixture was agitated for 2 hours and then filtered at a hot state. The filtrate was concentrated at 50° C. under reduced pressure, and the concentrated product in a paste form was dissolved in methanol. The solution was again concentrated at 40 to 45° C. under reduced pressure, and water was distilled off through azeotropy of methanol and water. The solution was further concentrated while adding methanol, and the deposited solid matter was filtered and dried to provide a purified product of HC Blue 15 (68.6 g, yield: 57.2%), which was the dye for hair coloration of the Comparative Example.

The resulting purified product of HC Blue 15 was subjected to the analysis at the start of the test and the storage stability tests under room temperature condition (6 months) and heating condition at 40° C. (7 days) in the same manner as in Example 1. The results are also shown in Table 1.

TABLE 1

| | | Purity (%) | | |
|---|---|---|---|---|
| | Measured component | Start of test | Room temperature test, 6 months | Heating test, 7 days |
| Example 1 (2-1) (AHC BLUE 77) | Dye | 99.0% | 99.0% | 99.0% |
| | Reddish impurity | 0.0% | 0.0% | 0.0% |
| Comparative Example 1 (2-1X) (HC BLUE 15) | Dye | 98.7% | 97.2% | 97.2% |
| | Reddish impurity | 0.0% | 0.8% | 1.4% |

It was found from Table 1 that in Example 1, the concentration ratio of the impurity derived from An was 1% by mass or less. In the room temperature test (6 months) and the heating test (7 days), there was no change in purity of the dye from the start of the test. The concentration ratio of the reddish impurity (0.0%) was also not changed from the start of the test. In Comparative Example 1, on the other hand, in the room temperature test, the purity of the dye was decreased, and the concentration ratio of the reddish impurity was increased. Furthermore, in the heating test, similarly, the purity of the dye was decreased, and the concentration ratio of the reddish impurity was increased. It was understood therefrom that the dye for hair coloration of the present invention was excellent in heat resistance (storage stability) as compared to the dye for hair coloration of Comparative Example 1.

Example 2

<Storage Stability Test of "Basic Yellow 40 Hydrochloride">

Basic Yellow 40 hydrochloride (available as a commercially available product from Nissei Kasei Co., Ltd.) was subjected to the storage stability test (heating test) in the same manner as in Example 1. The dye for hair coloration (Basic Yellow 40) represented by the following formula (G-3) was identified under the same HPLC measurement condition as in Example 1, and the HPLC purity thereof was 99.7%. The target yellow dye was measured as a peak of a retention time of 4.5 minutes, and the impurity component was measured as a peak of a retention time of 3.5 minutes, as the HPLC measurement components. The results are shown in Table 2 as the purity (concentration ratio) (%) at the start of the storage stability test.

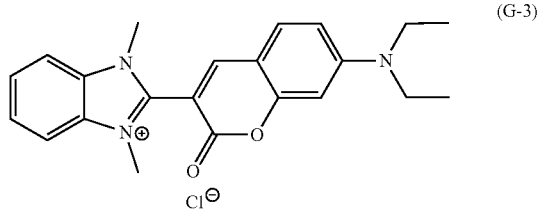 [SMILES: CCN(CC)c1ccc2cc(-c3n(C)c4ccccc4[n+]3C)c(=O)oc2c1 ; [Cl-]]

(Storage Stability Test under Heating Condition (Heating Test))

The solid powder specimen of Basic Yellow 40 hydrochloride placed in a resin bottle was heated to 50° C. for 7 days as similar to the heating test of AHC Blue 77 in Example 1. The powder specimen after heating for 7 days was measured for the dye and the impurity under the same HPLC condition as in Example 1. The results of the heating test (7 days) are shown in Table 2.

Comparative Example 2

Basic Yellow 40 methyl sulfate (represented by the following formula (G-3X) was subjected to the HPLC measurement in the same manner as in Example 2. As similar to Example 2, the target yellow dye was measured as a peak of a retention time of 4.5 minutes, and the impurity component was measured as a peak of a retention time of 3.5 minutes. The storage stability test was performed under heating condition at 50° C. for 7 days in the same manner as in Example 2. The results of the heating test (7 days) are also shown in Table 2.

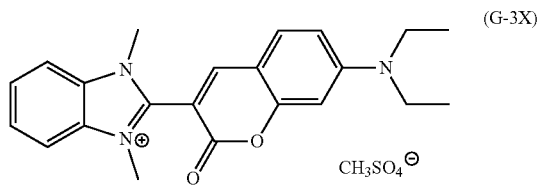

TABLE 2

| | | Purity (%) | |
| --- | --- | --- | --- |
| | Measured component | Start of test | Heating test, 7 days |
| Example 2 (G-3) (Basic Yellow 40 Cl⁻) | Dye | 99.7% | 99.6% |
| | Impurity | 0.2% | 0.2% |
| Comparative Example 2 (G-3X) (Basic Yellow 40 CH₃SO₄⁻) | Dye | 99.1% | 98.0% |
| | Impurity | 0.5% | 1.2% |

It was found from Table 2 that in Example 2, the concentration ratio of the impurity derived from An was 1% by mass or less. In the heating test (7 days), there was no change in purity of the dye. The concentration ratio of the impurity component was also not changed. In Comparative Example 2, on the other hand, after the heating test, the purity of the dye was decreased, and the concentration ratio of the impurity component was increased. It was understood therefrom that the dye for hair coloration of the present invention was excellent in heat resistance (storage stability) as compared to the dye for hair coloration of Comparative Example.

Example 3

<Production of Dyed Hair Specimen and Heat Resistance Test>

0.04 g of the dye for hair coloration (formula (2-1)), 18.3 g of a pH 6 aqueous solution (prepared by diluting 1 g of citric acid monohydrate and 11 g of trisodium citrate dihydrate with water to make 1,000 mL in a measuring flask) as a pH modifier (pH buffer), 0.2 g of trimethylstearylammonium chloride (TMSA) as a surfactant, 1.0 g of ethanol, and 0.5 g of benzyl alcohol as a penetrating agent were mixed and dissolved. 1.0 g (2 threads) of artificial white hair (product name: White Hair 100% BM-W, available from Beaulax Co., Ltd.) was placed in the resulting solution, and dyed at 40° C. for 20 minutes, washed with water, and spontaneously dried to provide a dyed test specimen (dyed hair specimen).

The color tone (L*, a*, b*) of the resulting dyed hair specimen was measured for the CIE L*a*b* color system with a spectrocolorimeter (JS555, available from Color Techno System Corporation). The color difference ΔE* was calculated from the values of ΔL*, Δa*, and Δb* according to the following expression.

$$\Delta E^* = \{(\Delta L^*)^2 + (\Delta a^*)^2 + (\Delta b^*)^2\}^{1/2}$$

The dyed hair specimen was heated with a hot air dryer (which was the same dryer as used in Example 1) to 50° C. for 7 days. As a result of the heat resistance test of the dyed hair specimen, the measurement results of the color tone of the dyed hair specimen before and after heating and the resulting value of the color difference ΔE* are shown in Table 3.

Example 4

The production of the dyed hair specimen and the heat resistance test thereof were performed in the same manner as in Example 3 except that the dye for hair coloration (formula (G-3)) was used instead of the dye for hair coloration (formula (2-1)) in Example 3. The results are also shown in Table 3.

Comparative Example 3

The production of the dyed hair specimen and the heat resistance test thereof were performed in the same manner as in Example 3 except that the dye for hair coloration (formula (2-1X)) was used instead of the dye for hair coloration (formula (2-1)) in Example 3. The results are also shown in Table 3.

Comparative Example 4

The production of the dyed hair specimen and the heat resistance test thereof were performed in the same manner as in Example 3 except that the dye for hair coloration (formula (G-3X)) was used instead of the dye for hair coloration (formula (2-1)) in Example 3. The results are also shown in Table 3.

TABLE 3

| | Dye | Heating | L* | a* | b* | Δa | Δb | Color difference ΔE* |
|---|---|---|---|---|---|---|---|---|
| Example 3 | (2-1) | Before | 22.89 | −1.12 | −22.11 | — | — | — |
| | | After | 23.32 | −2.01 | −21.94 | −0.89 | 0.17 | 1.00 |
| Comparative Example 3 | (2-1X) | Before | 19.56 | −3.79 | −18.58 | — | — | — |
| | | After | 19.33 | −0.85 | −22.10 | 2.94 | −3.52 | 4.59 |
| Example 4 | (G-3) | Before | 54.53 | −4.60 | 56.64 | — | — | — |
| | | After | 54.98 | −5.33 | 56.50 | −0.73 | −0.14 | 0.87 |
| Comparative Example 4 | (G-3X) | Before | 56.94 | −5.16 | 61.00 | — | — | — |
| | | After | 53.74 | −4.23 | 57.91 | 0.93 | −3.09 | 4.54 |

It was understood from the results in Table 3 that the color difference before and after the heat resistance test of the dyed hair specimen was smaller in Examples 3 and 4 than in Comparative Examples 3 and 4, and the hair dyed with the dye for hair coloration of the present invention exerted the effect of suppressing decoloration due to heating, as compared to the hair dyed with the dyes in Comparative Examples 3 and 4.

INDUSTRIAL APPLICABILITY

According to the dye for hair coloration and the method for producing a dye for hair coloration of the present invention, a dye for hair coloration that has a longer shelf life than the ordinary dye for hair coloration and is excellent in heat resistance can be obtained. Furthermore, according to the composition for hair coloration containing the dye for hair coloration of the present invention, a hair colorant that can effectively suppress decoloration of dyed hair can be provided.

The invention claimed is:

1. A dye for hair coloration represented by the following general formula (1), the dye for hair coloration having a proportion of a polyatomic anion (An) or impurities derived from An of 1% by mass or less:

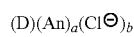

(D)(An)$_a$(Cl$^\ominus$)$_b$ (1)

wherein in the formula (1), D represents a cationic moiety of the dye for hair coloration; An represents a polyatomic anion; b>0; and a>0.

2. The dye for hair coloration according to claim 1, wherein in the general formula (1), D represents a cationic moiety of a triarylmethane dye, a xanthene dye, a phenothiazine dye, a phenazine dye, a phenoxazine dye, an azo dye, an azomethine dye, or an HC dye.

3. The dye for hair coloration according to claim 1, wherein in the general formula (1), D is represented by the following general formula (2):

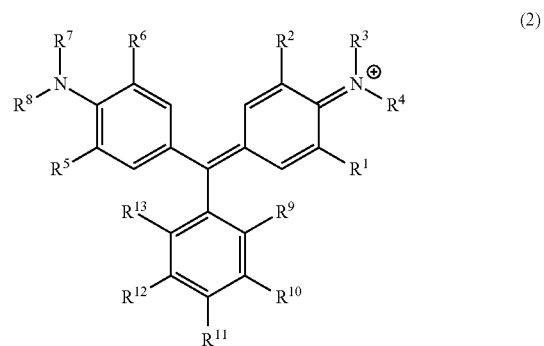

wherein in the formula (2), 1e to R″ each independently represent —H, a halogen atom, —NO$_2$, —NO, —CN, —OH, an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that adjacent groups of each combination of R$^3$ and R$^4$, R$^7$ and R$^8$, and R$^9$ to R$^{13}$ may be bonded to each other to form a ring.

4. The dye for hair coloration according to claim 1, wherein in the general formula (1), D is represented by the following general formula (3):

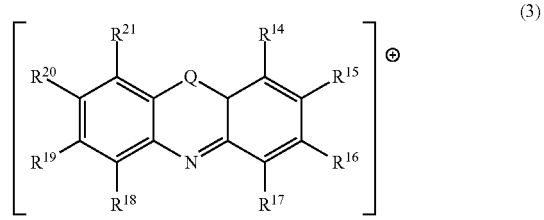

wherein in the formula (3), $R^{14}$ to $R^{21}$ each independently represent —H, a halogen atom, —NO$_2$, —NO, —CN, —OH, an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that adjacent groups of $R^{14}$ to $R^{21}$ may be bonded to each other to form a ring; and Q represents —CH=, —N=, —O—, —S—, an amino group having 0 to 30 carbon atoms, which may have a substituent, or a methylene group, which may have a substituent.

5. The dye for hair coloration according to claim 1, wherein in the general formula (1), D is represented by the following general formula (4):

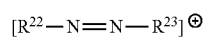   (4)

[$R^{22}$—N=N—$R^{23}$]$^{\oplus}$ wherein in the formula (4), $R^{22}$ and $R^{23}$ each represent an amino group having 0 to 20 carbon atoms, which may have a substituent, a linear or branched alkenyl group having 2 to 20 carbon atoms, which may have a substituent, an aromatic hydrocarbon group having 6 to 30 carbon atoms, which may have a substituent, or a heterocyclic group having 2 to 30 carbon atoms, which may have a substituent.

6. The dye for hair coloration according to claim 1, wherein in the general formula (1), D is represented by the following general formula (5):

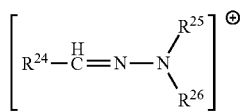   (5)

wherein in the formula (5), $R^{24}$ to $R^{26}$ each independently represent an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that $R^{25}$ and $R^{26}$ may be bonded to each other to form a ring.

7. The dye for hair coloration according to claim 3, wherein in the general formula (2), $R^1$, $R^2$, $R^5$, and $R^6$ each represent —H or a methyl group; $R^3$, $R^4$, $R^7$, and $R^8$ each represent —H, a methyl group, or an ethyl group; and $R^9$ to $R^{13}$ each represent —H, —Cl, an amino group having 0 to 10 carbon atoms, which may have a substituent, an alkenyl group having 2 to 10 carbon atoms, which may have a substituent, an alkyl group having 1 to 10 carbon atoms, which may have a substituent, or an acyl group having 1 to 10 carbon atoms, which may have a substituent.

8. The dye for hair coloration according to claim 1, wherein in the general formula (1), An represents a hydrogen-containing anion.

9. The dye for hair coloration according to claim 1, wherein the dye for hair coloration has a shelf life of 6 months or more at a room temperature (20 to 25° C.) or 7 days or more at a 40 to 60° C.

10. A composition for hair coloration comprising the dye for hair coloration according to claim 1, at least one kind of an auxiliary agent selected from the group consisting of a wetting agent, a swelling agent, a penetrating agent, a solvent, a pH modifier, a surfactant, a perfume, and a thickener, and water.

11. A method for producing a dye for hair coloration represented by the following general formula (6)

   (6)

(D)(An)$_a$(Cl$^{\ominus}$)$_b$ wherein in the formula (6), D represents a cationic moiety of the dye for hair coloration; An represents a polyatomic anion; and a and b each independently represent a value of 0 to 1, the method comprising:

purifying a dye for hair coloration containing a polyatomic anion (An) with water and activated carbon to obtain a purified dye; and dissolving the purified dye with water and salt, and then performing salt exchange.

12. The method of claim 11, wherein a>0 and b>0.

13. The method of claim 11, wherein b>a and a>0.

14. The method of claim 11, wherein in the general formula (6), D represents a cationic moiety of a triarylmethane dye, a xanthene dye, a phenothiazine dye, a phenazine dye, a phenoxazine dye, an azo dye, an azomethine dye, or an HC dye.

15. The method of claim 11, wherein in the general formula (6), D is represented by the following general formula (2):

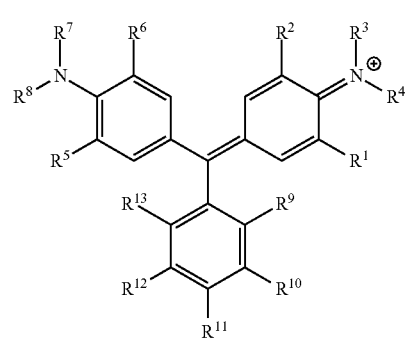   (2)

wherein in the formula (2), $R^1$ to $R^{13}$ each independently represent —H, a halogen atom, —NO$_2$, —NO, —CN, —OH, an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that adjacent groups of each combination of $R^3$ and $R^4$, $R^7$ and $R^8$, and $R^9$ to $R^{13}$ may be bonded to each other to form a ring.

16. The method of claim 11, wherein in the general formula (6), D is represented by the following general formula (3):

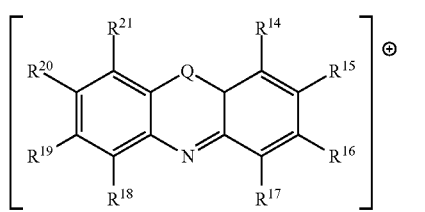

(3)

wherein in the formula (3), $R^{14}$ to $R^{21}$ each independently represent —H, a halogen atom, —NO$_2$, —NO, —CN, —OH, an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that adjacent groups of $R^{14}$ to $R^{21}$ may be bonded to each other to form a ring; and Q represents —CH=, —N=, —O—, —S—, an amino group having 0 to 30 carbon atoms, which may have a substituent, or a methylene group, which may have a substituent.

17. The method of claim 11, wherein in the general formula (6), D is represented by the following general formula (4):

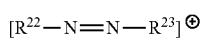

(4)

wherein in the formula (4), $R^{22}$ and $R^{23}$ each represent an amino group having 0 to 20 carbon atoms, which may have a substituent, a linear or branched alkenyl group having 2 to 20 carbon atoms, which may have a substituent, an aromatic hydrocarbon group having 6 to 30 carbon atoms, which may have a substituent, or a heterocyclic group having 2 to 30 carbon atoms, which may have a substituent.

18. The method of claim 11, wherein in the general formula (6), D is represented by the following general formula (5):

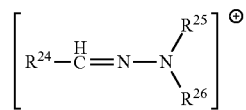

(5)

wherein in the formula (5), $R^{24}$ to $R^{26}$ each independently represent an amino group having 0 to 20 carbon atoms, which may have a substituent, a linear or branched alkenyl group having 2 to 20 carbon atoms, which may have a substituent, a linear or branched alkyl group having 1 to 20 carbon atoms, which may have a substituent, a linear or branched alkoxy group having 1 to 20 carbon atoms, which may have a substituent, an acyl group having 1 to 20 carbon atoms, which may have a substituent, an aromatic hydrocarbon group having 6 to 30 carbon atoms, which may have a substituent, or a heterocyclic group having 2 to 30 carbon atoms, which may have a substituent, provided that $R^{25}$ and $R^{26}$ may be bonded to each other to form a ring.

19. The method of claim 11, wherein in the general formula (6), An represents a hydrogen-containing anion.

20. The dye for hair coloration of claim 1, wherein b>a.

* * * * *

UNITED STATES PATENT AND TRADEMARK OFFICE
CERTIFICATE OF CORRECTION

PATENT NO. : 11,273,110 B2
APPLICATION NO. : 17/185192
DATED : March 15, 2022
INVENTOR(S) : Naito et al.

It is certified that error appears in the above-identified patent and that said Letters Patent is hereby corrected as shown below:

In the Claims

At Column 32, Line 38 (Claim 3, Line 5), please change "$R^n$" to -- $R^{13}$ --.

Signed and Sealed this
Twenty-third Day of August, 2022

Katherine Kelly Vidal
*Director of the United States Patent and Trademark Office*